(12) United States Patent
Kirkpatrick et al.

(10) Patent No.: US 7,629,128 B2
(45) Date of Patent: Dec. 8, 2009

(54) METHODS OF IDENTIFYING RESPONDENTS TO HYPOXIA INDUCIBLE FACTOR 1-α INHIBITORS

(75) Inventors: Lynn Kirkpatrick, Houston, TX (US); Linda Anne Pestano, Oro Valley, AZ (US)

(73) Assignee: Prolx Pharmaceuticals Corp., Tucson, AZ (US)

( * ) Notice: Subject to any disclaimer, the term of this patent is extended or adjusted under 35 U.S.C. 154(b) by 283 days.

(21) Appl. No.: 11/379,034

(22) Filed: Apr. 17, 2006

(65) Prior Publication Data

US 2006/0275836 A1 Dec. 7, 2006

Related U.S. Application Data

(63) Continuation-in-part of application No. 10/929,156, filed on Aug. 30, 2004, now Pat. No. 7,399,785.

(60) Provisional application No. 60/671,765, filed on Apr. 15, 2005.

(51) Int. Cl.
*G01N 33/53* (2006.01)
*C07K 16/00* (2006.01)

(52) U.S. Cl. ............ 435/7.1; 435/7.24; 530/387.1

(58) Field of Classification Search ............... None
See application file for complete search history.

(56) References Cited

U.S. PATENT DOCUMENTS 5,602,278 A 2/1997 Kirkpatrick

OTHER PUBLICATIONS

Vordermark et al. Evaluation of hypoxia-inducible factor-1alpha (HIF-1alpha) as an intrinsic marker of tumor hypoxia in U87 MG human glioblastoma: in vitro and xenograft studies. Int J Radiat Oncol Biol Phys. Jul. 15, 2003;56(4):1184-93.*

Makino et al. Hypoxia-inducible factor regulates survival of antigen receptor-driven T cells. J Immunol. Dec. 15, 2003;171(12):6534-40.*

Lim et al. Ras-dependent induction of HIF-1alpha785 via the Raf/MEK/ERK pathway: a novel mechanism of Ras-mediated tumor promotion. Oncogene. Dec. 16, 2004;23(58):9427-31.*

Carraro et al. p66Shc is involved in promoting HIF-1alpha accumulation and cell death in hypoxic T cells. J Cell Physiol. May 2007;211(2):439-47.*

Lukashev et al. Differential regulation of two alternatively spliced isoforms of hypoxia-inducible factor-1 alpha in activated T lymphocytes. J Biol Chem. Dec. 28, 2001;276(52):48754-63.*

Mendis et al. Transcriptional response signature of human lymphoid cells to staphylococcal enterotoxin B. Genes Immun. Mar. 2005;6(2):84-94.*

Zhou et al. NO and TNF-alpha released from activated macrophages stabilize HIF-1alpha in resting tubular LLC-PK1 cells. Am J Physiol Cell Physiol. Feb. 2003;284(2):C439-46.*

Powis, et al., Hypoxic inducible factor-1α as a cancer drug test, 2004, Mol. Cancer Ther. 3(5):647-654.

Welsh et al., PX-478—A Potent Inhibitor of Hypoxia-Inducible Factor-1 and Anti-Tumor Agent, Nov. 19-22, 2002, AACR-EORTC-NCI Meeting, Frankfurt, Germany.

Zalgeviciene et al., Embryotoxicity and teratogenicity of some derivatives of chloroethylaminophenylacetic acid, Pathology Onc. Res. 4(1):27-29, 1998.

Breivis et al., Faranoxi—A new antitumor agent, J. of Chemo. 8(1):67-69, 1996.

Kirkpatrick et al., Synthesis and bioreductive potential of a mono N-oxide derivative of the alkylating agent chlorambucil, 1994, Anti-Cancer Drugs 5:467-472.

* cited by examiner

*Primary Examiner*—Maher M Haddad
(74) *Attorney, Agent, or Firm*—Pepper Hamilton LLP

(57) ABSTRACT

This invention relates to methods of measuring HIF expression and activity, as well as measuring inhibition of HIF following administration of an HIF inhibitor useful in treating HIF related diseases. The present invention further relates to methods of identifying individuals who will respond to HIF inhibitors. The invention also relates to methods of monitoring a patient response to a given dosage of an HIF inhibitor. The invention also includes assays and kits for performing the methods described herein.

5 Claims, 18 Drawing Sheets

A

B

Primary Peripheral Blood Mononuclear Cells

Jurkat Acute Lymphocytic Leukemia Cell Line

METHODS OF IDENTIFYING RESPONDENTS TO HYPOXIA INDUCIBLE FACTOR 1-α INHIBITORS

CROSS REFERENCE TO RELATED APPLICATIONS

This application is a continuation in part of U.S. Ser. No. 10/929,156, now U.S Pat. No. 7,399,785, filed Aug. 30, 2004, and claims the benefit of U.S. Provisional Application No. 60/671,765, filed Apr. 15, 2005, the contents of which are both incorporated herein by reference in their entirety.

REFERENCE TO GOVERNMENT GRANT

This invention was made with government support under U19 CA052995, U54 CA090821 and RO1 CA098920 awarded by NIH. The government has certain rights in this invention.

STATEMENT REGARDING FEDERALLY SPONSORED RESEARCH OR DEVELOPMENT

NOT APPLICABLE

JOINT RESEARCH AGREEMENT

NOT APPLICABLE

INCORPORATION BY REFERENCE OF MATERIAL SUBMITTED ON A CD

NOT APPLICABLE

BACKGROUND OF THE INVENTION

Hypoxia inducible factor-1 (HIF-1) plays a central role in the development and progression of tumors. While not wishing to be bound by theory, it appears this is because HIF-1 controls the expression of more than 40 target genes whose protein products play crucial roles in allowing the survival of cells under adverse environmental conditions and in response to radiation or chemotherapy. These include the gene encoding VEGF, which is required for tumor angiogenesis, insulin-like growth factor 2 (IGF2), which promotes tumor cell survival, and glucose transporters 1 and 3, and glycolytic enzymes such as aldolase A and C, hexokinase 1 and 3, lactate dehydrogenase A and PGK.

HIF-1α is a subunit of HIF-1. HIF-1α protein is found in a wide variety of human primary tumors but only at very low levels in normal tissue. The importance of HIF-1α to cancer is demonstrated by the high incidence of tumors such as renal cell carcinoma, pheochromocytoma and hemingioblastoma of the central nervous system in individuals with loss of function of both alleles of the VHL gene leading to elevated HIF-1α levels. In addition, most cases of sporadic renal cell carcinoma are associated with an early loss of function of the VHL gene and increased HIF-1α levels. Reintroduction of the intact VHL gene into cells derived from renal carcinomas restores HIF-1α to normoxic levels and decreases tumorigenicity. HIF-1α levels are also increased in cancer cells with mutant or deleted PTEN.

Many human tumors have been shown to overexpress HIF-1α protein as a result of intratumoral hypoxia and genetic alterations affecting key oncogenes and tumor suppressor genes. In addition, over-expression of HIF-1α correlates with treatment failure and mortality. However, loss of HIF-1 activity has dramatic negative effects on tumor growth, vascularization and energy metabolism in xenograft assays. Therefore inhibition of HIF-1 represents a promising new approach to cancer therapy since its inhibition may lead to the selective killing of tumor cells over normal cells.

The HIF-1α inhibitor PX-478 (S-2-amino-3-[4'-N,N,-bis (2-chloroethyl)amino]phenyl propionic acid N-oxide dihydrochloride) inhibits growth of hypoxic tumor cells in vitro. PX-478 inhibits HIF-1α protein, leading to decreased HIF-1 transactivation and expression of the downstream target gene VEGF. PX-478 also decreases HIF-1α in vivo at a non-toxic dose. Interestingly, this inhibition has been shown to occur independently of the VHL pathway, the most well-studied mechanism for controlling HIF-1α stabilization.

Many other factors have been shown to affect HIF-1α protein, including the P53 tumor suppressor pathway as well as oncogenes signalling through the P13K and MAPK pathways. Several recent studies have also reported indirect inhibition of the HIF-1 pathway in a VHL independent manner. These include inhibition of P13K using LY294002, inhibition of the molecular chaperone HSP90 using geldanaycin, and inhibition of redox signalling by PX-12 (1-methylpropyl 2-imidazolyl disulfide) and pleurotin. Indeed, thioredoxin reductase activity was shown in this study to be significantly decreased at concentrations of PX-478 which correlate well with HIF-1α inhibition.

A recent study has shown that Trx-1 binds to, and inhibits, the tumor-suppressor protein PTEN leading to activation of the P13K pathway through AKT. In light of the findings that the P13K/AKT pathway is involved in the stabilization and activation of HIF and that the P13K inhibitor LY294002 also decreases HIF-1α protein in a VHL independent manner, it is possible Trx-1 may affect HIF-1α through this pathway. Recent studies suggest that this is cell-type dependent and, when observed, lies downstream of HIF activation or in a parallel pathway.

One goal of targeted therapies for disease treatment, such as the HIF-1α inhibitor PX478 in treating cancer, is to be able to select patients that are most likely to respond to the drug. In the case of cancer, while immunohistochemical techniques verifying the upregulation of HIF-1α in the target tumor is the gold standard, often invasive procedures such as tumor biopsies are not possible and the tumor tissue required for such tests are not available. Non-invasive techniques have been explored to evaluate the effect of PX478 on HIF-1α levels in the clinical setting, including the use of Dynamic Contract Enhanced-magnetic resonance imaging (DCE-MRI) and diffusion weighted (DW) MRI to evaluate tumor vascular permeability. It is possible that even though a tumor may express some level of HIF-1α, the protein some patients express may not be responsive to a synthetic inhibitor such as PX-478. In order to provide effective treatment to an individual, it would be helpful to identify those individuals who will be responsive or susceptible to an HIF inhibitor (e.g., PX-12, PX-478, 2-ME2). It would be useful to be able to identify patients with hypoxic tumors and corresponding increased HIF-1α levels, and to be able to evaluate the HIF-1α inhibition following therapy.

SUMMARY OF THE INVENTION

In one embodiment, a method of identifying an individual susceptible to treatment with a HIF-1α inhibitor is provided. The method may comprise the steps of obtaining a blood sample from said individual; exposing the blood sample to a leukocyte stimulating agent to the blood sample; measuring a second level of HIF in the blood sample; and identifying an individual who is susceptible to treatment with a HIF-1α inhibitor, wherein elevated levels of HIF indicate said individual's susceptibility to said treatment with said HIF-1α inhibitor. In preferred embodiments, the HIF-1α inhibitor is PX-478 or PX-12. In another embodiment, the method may further comprise the step of separating or isolating PBMC from the blood sample. In another embodiment, the method may further comprise the step of inducing a hypoxic condition in the blood sample.

In a further embodiment, a method of determining efficacy of a HIF-1α inhibitor therapy is provided. The method may comprise the steps of obtaining a first blood sample from said individual; exposing the first blood sample to a first leukocyte stimulating agent; measuring a level of HIF in said first blood sample; and identifying said individual susceptible to treatment, wherein elevated levels of HIF indicate said individual's susceptibility to said treatment with said HIF-1α inhibitor; administering a HIF-1α inhibitor to said individual; obtaining a second blood sample from said individual; exposing said second blood sample to a second leukocyte stimulating agent; measuring a second level of HIF expression in said blood sample, wherein decreased levels of HIF indicates effective HIF-1α inhibitor therapy.

In another embodiment, a method of determining efficacy of a HIF-1α inhibitor therapy in an individual is also provided. The method may comprise obtaining a first blood sample from said individual; measuring a first level of HIF in said blood sample; administering a HIF-1α inhibitor to said individual; obtaining a second blood sample from said individual; exposing said blood sample to a leukocyte stimulating agent and hypoxic conditions; and measuring a second level of HIF in said second blood sample, wherein decreased levels of HIF indicates effective HIF-1α inhibitor therapy.

BRIEF DESCRIPTION OF THE FIGURES

The file of this patent contains at least one drawing executed in color. Copies of this patent with color drawing(s) will be provided by the Patent and Trademark Office upon request and payment of necessary fee.

Various aspects and applications of the present invention will become apparent to the skilled artisan upon consideration of the brief description of the figures and the detailed description of the invention, which follows.

DETAILED DESCRIPTION OF THE INVENTION

Figure 1:
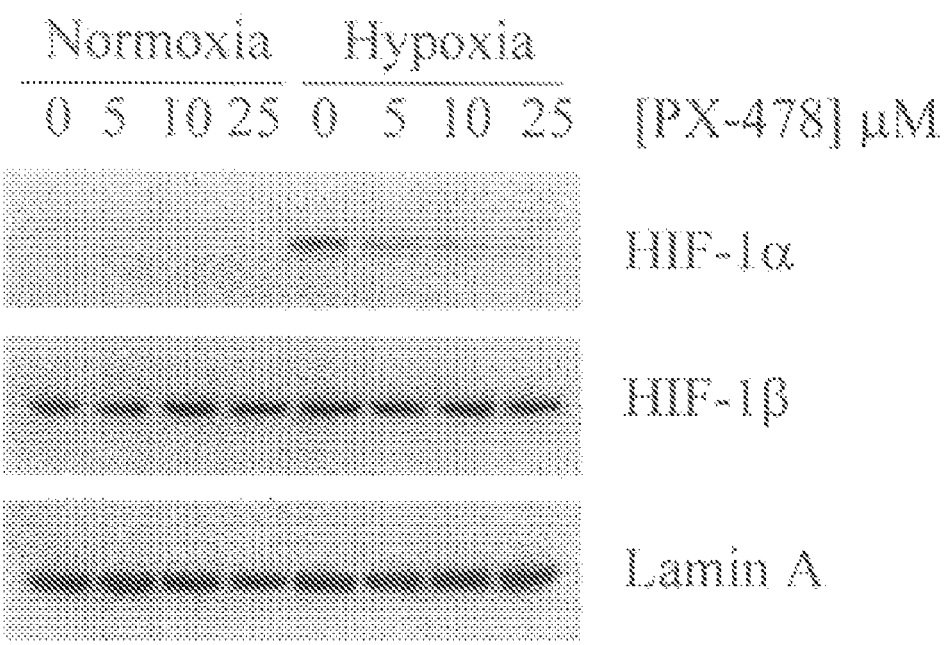
FIGS. 1A and 1B illustrate the effect of PX-478 on HIF-1α and HIF-1β protein levels.
Figure 1:
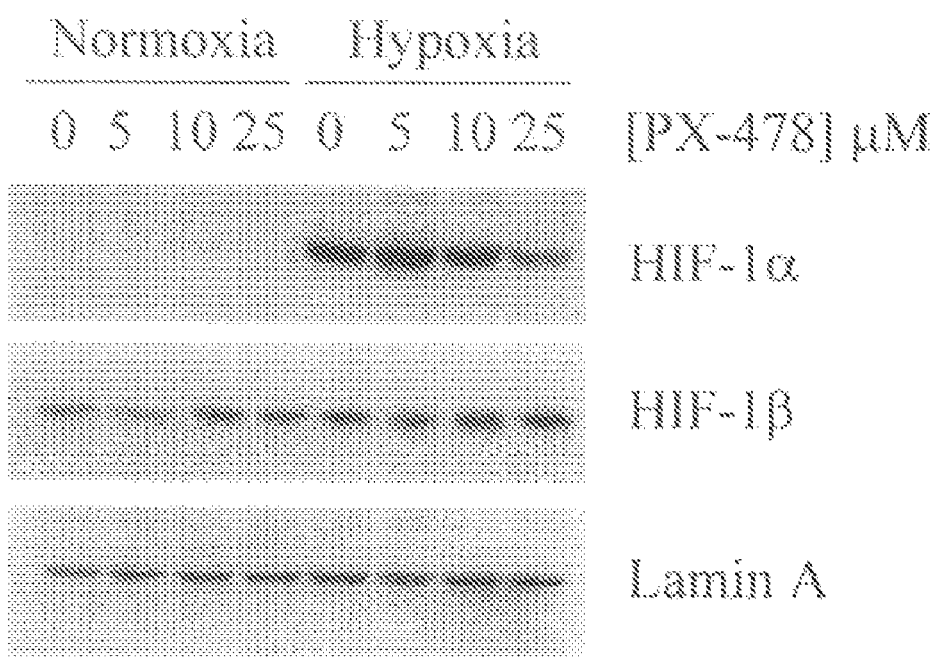

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

One aspect of the present invention relates to assays to measure expression or activity levels of an HIF, preferably HIF-1α. In certain embodiments, the assay comprises obtaining a sample of an individual's peripheral blood, inducing a hypoxic condition in at least one cell of the sample, and measuring the response of one or more of the individual's peripheral blood mononuclear cells (PBMCs) or leukocytes to the hypoxic condition. In a preferred embodiment, the assay comprises measuring the response in a population or subset of PBMC or leukocytes obtained from an individual's blood to a hypoxic condition. In certain embodiments, the assay comprises obtaining a sample of an individual's peripheral blood, separating one or more cells obtained from a population of the individual's leukocytes from the blood sample, inducing a hypoxic condition in the cell or cells, and measuring the response of the cell or cells to the hypoxic condition. In further embodiments, the assay comprises measuring the response of the cell or cells to HIF inhibitors, including, for example, N-oxide and derivatives thereof, and agents which inhibit HIF through inhibition of other pathways including, but not limited to, inhibition of thioredoxin or thioredoxin reductase, P13 kinase or AKT.

The cell or cells obtained from a population of PBMCs or leukocytes may include one or more types of blood cells, for example, one or more of T cells, B cells, NK cells, and monocytes, in any combination. In one embodiment, the method of the invention comprises measuring a response to stimulation and hypoxia in at least one leukocyte. In another embodiment, the method of the invention comprises measuring a response to stimulation and hypoxia in at least one T cell.

According to the invention, the method comprises measuring a response in one or more blood cells of an individual to a hypoxic condition. The measuring step generally involves detecting the expression or activity of an HIF. The measuring step may include, for example, measuring expression or activity of an HIF-1 protein, or may include measuring expression of an HIF gene in one or more blood cells. The measuring step may be performed by a variety of methods, including, for example, by flow cytometry.

A "hypoxic condition" refers to a state of oxygen deficiency sufficient to cause impairment of function. Preferably a hypoxic condition is created by exposure to about 1% oxygen. Cells are normally exposed to about 20% oxygen. A hypoxic condition can be induced in blood cells by a variety of methods known in the art, including methods demonstrated in the Examples, below, including but not limited to administration or exposure to DFO.

In further aspects, the invention relates to identifying subjects that may be responsive to HIF inhibitors, for example PX-478, and other N-oxides or derivatives thereof, PX-12, 2-ME2, topotecan and camptothecin or derivatives thereof. HIF inhibitors include agents that inhibit HIF, e.g., agents that inhibit HIF-1α. Such inhibition may be direct or indirect. That is, the inhibitor may act directly on an HIF gene or protein molecule to inhibit its expression or activity. However, the inhibitor may act indirectly by affecting expression or activity of another molecule which ultimately leads to inhibition of expression or activity of an HIF gene or protein molecule. In certain aspects, therapy includes administration of an HIF inhibitor, including, but not limited to, an HIF inhibitor discussed herein or any of the HIF inhibitors discussed in Powis, G. and Kirkpatrick, L., Hypoxic inducible factor-1α as a cancer drug target, *Mol. Cancer Ther.* 3(5):647-654 (2004), which is hereby incorporated by reference in its entirety. The invention, however, is not limited to evaluating HIF inhibition caused by known HIF inhibitors; rather, it can be applied to evaluate any HIF inhibitor.

Diseases that may be treated by directly or indirectly inhibiting HIF, particularly HIF-1α, include diseases associated with angiogenesis or neovascularization. Diseases associated with HIF, or cells relying on HIF for survival, which may be treated with HIF inhibitors include cancer, ischemic myocardial and limb disease, ischemic stroke, Alzheimer's disease, choroidal and retinal neovascularization, age-related macular degeneration, joint disease, inflammation, neurodegenerative diseases, autoimmunity, infectious disease and ischemic reperfusion injury.

According to some aspects of the invention, the method further comprises treating at least one leukocyte of a blood sample from an individual with an HIF inhibitor prior to measuring the response of the at least one leukocyte to a hypoxic condition. The HIF inhibitor may be one of a variety of HIF inhibitors as discussed herein. In one embodiment, the HIF inhibitor is PX-478. In other embodiments, the HIF inhibitor is PX-12.

The invention comprises, in some aspects, obtaining a first subset of at least one leukocyte from a blood sample, obtaining a second subset of at least one leukocyte from the blood sample, and treating either the first or second subset with an HIF inhibitor. According to this embodiment, the measuring step then comprises measuring HIF protein level or activity in the two subsets. The invention may further comprise comparing the HIF protein level or activity of the first and second subsets.

Generally, a normal donor's PBMCs, once stimulated with phorbol myristate acetate (PMA) and calcium ionophore A23187, will upregulate HIF-1α expression under normoxic conditions. This HIF-1α accumulation can typically be enhanced under hypoxia and is sensitive to PX-478 exposure. However, as described in the Examples, we have identified donors whose PBMCs did not upregulate HIF-1α upon stimulation alone and required a second signal such as hypoxia to visualize HIF-1α accumulation by flow cytometry. The addition of PX-478 added directly to the donor's whole blood one hour before the isolation of the PBMC and subsequent stimulation with PMA/ionophore and DFO had no effect on the HIF-1α levels under conditions that lowered the HIF-1α expression of two normal donors by at least 50%.

Therefore, we have developed assays capable of distinguishing between individuals whose HIF-1α levels in PBMCs can be stimulated and that respond to PX-478 or other HIF inhibitors, versus those whose cells are not responsive. The HIF-1α response of the PBMCs to stimulation and hypoxia, and/or the response to PX-478 using such an assay provides a test a priori that can identify patients that are likely to benefit by treatment with an HIF-1α inhibitor. Additionally, we have developed an assay to monitor patient response to an HIF inhibitor.

A further aspect of the present invention is to clinically evaluate HIF inhibition, e.g., HIF-1α inhibition, following therapy. One embodiment comprises, therefore, a method of monitoring patient response to a HIF inhibitor. The method comprises obtaining a first sample of a patient's blood, treating the patient with an HIF inhibitor, obtaining a second sample of the patient's blood, inducing a hypoxic condition in the blood samples, measuring a response to the hypoxic condition in at least one leukocyte of the blood samples, and comparing the responses of the blood samples. Depending on the response observed, a patient's therapy using a given HIF inhibitor may be modified, for example, the dosage may be increased or decreased or the frequency of dosing may be increased or decreased.

In a further embodiment, a method of identifying an individual susceptible to treatment with a HIF-1α inhibitor is provided. The method may comprise the steps of obtaining a blood sample from said individual; measuring a first level of HIF in the blood sample; administering a T cell stimulating agent to the blood sample; measuring a second level of HIF in the blood sample; and identifying an individual who is susceptible to treatment with a HIF-1α inhibitor, wherein elevated levels of HIF indicate said individual's susceptibility to said treatment with said HIF-1α inhibitor. In preferred embodiments, the HIF-1α inhibitor is PX-478 or PX-12. In another embodiment, the method may further comprise the step of inducing a hypoxic condition in the blood sample.

The leukocyte stimulating agent may be any agent capable of stimulating T cells and/or B cells. For example, the leukocyte stimulating agent may be an antibody or a mitogen. Mitogens are agents that are able to induce cell division (mitosis) in T cells and/or B cells. Preferably mitogens include lectins, such as concanavalin A (Con A), phytohemagglutinin (PHA) and pokeweed mitogen (PWM), and lipopolysaccharide or endotoxin (LPS). Superantigens are potent T cell mitogens, which may also be a T cell stimulating agent. Exemplary superantigens include staphylococcal exotoxins, such as staphylococcal toxic shock syndrome toxin 1 and staphylococcal enterotoxins A and B (SEA and SEB, respectively. In preferred embodiments, the leukocyte stimulating agent may be selected from phorbol myristate acetate, calcium ionophore, concanavalin A, anti-CD3 antibody, anti-CD28 antibody, PHA and combinations thereof.

HIF levels may be measured by measuring levels of HIF protein expression or HIF gene expression. Preferably, the step of measuring comprises measuring expression of a HIF-1α protein. Elevated levels of HIF are about at least a 2-fold increase of HIF over a baseline level. Baseline levels of HIF may be obtained from the specific individual or from an average of normal levels of HIF.

In another embodiment, a method of determining efficacy of a HIF-1α inhibitor therapy is provided. The method may comprise the steps of obtaining a first blood sample from said individual; measuring a first level of HIF in said blood sample; exposing said blood sample to a first leukocyte stimulating agent; measuring a second level of HIF in said first blood sample; and identifying said individual susceptible to treatment, wherein elevated levels of HIF indicate said individual's susceptibility to said treatment with said HIF-1α inhibitor; administering a HIF-1α inhibitor to said individual; obtaining a second blood sample from said individual; administering a second T cell stimulating agent; measuring a third level of HIF expression in said blood sample, wherein decreased levels of HIF indicates effective HIF-1α inhibitor therapy.

A method of determining efficacy of a HIF-1α inhibitor therapy in an individual is also provided. The method may comprise obtaining a first blood sample from said individual; measuring a first level of HIF in said blood sample; administering a HIF-1α inhibitor to said individual; obtaining a second blood sample from said individual; exposing said blood sample to a leukocyte stimulating agent and hypoxic conditions to said blood sample; and measuring a second level of HIF in said second blood sample, wherein decreased levels of HIF indicates effective HIF-1α inhibitor therapy.

The invention further comprises kits or assays. In one embodiment, a kit or assay comprises a component for obtaining a blood sample from an individual, a component for inducing a hypoxic condition in the blood sample or subset thereof, a component for measuring a response to said hypoxic condition in the blood sample or subset thereof, and a component for identifying an individual susceptible to treatment.

According to another embodiment, the kit or assay of the invention comprises a component for obtaining a blood sample from an individual, a component for separating one or more leukocyte cells from the blood, a component for inducing a hypoxic condition in said one or more leukocyte cells, a component for measuring a response to hypoxia in the one or more leukocyte cells, and a component for identifying said individual susceptible to treatment. The kit or assay of the invention may also include a component for measuring expression of an HIF-1α protein in said at least one leukocyte. The kit or assay of the invention may also include a component for measuring expression of HIF-1α protein using flow cytometry.

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention and do not delimit the scope of the invention. Various modifications and combinations of the illustrative embodiments, as well as other embodiments of the invention, will be apparent to persons skilled in the art upon reference to the description.

EXAMPLE 1

Cell culture and hypoxia treatment. MCF-7 human breast cancer and HT-29 colon cancer cells were obtained from the American Tissue Type Collection. Cells were grown under humidified 95% air, 5% $CO_2$ incubator at 37° C. in Dulbecco's modified Eagle's medium (DMEM) supplemented with 10% fetal bovine serum (FBS), and 1 mg/ml G418 where appropriate. For exposure to hypoxia the culture flasks were incubated for various times in a humidified chamber at 37° C. with a gas mixture containing 5% $CO_2$/74% $N_2$/21% argon. Oxygen levels were kept at 1% in the gas phase using an oxygen sensor (Pro:Ox 110, Biospherix, Redfield, N.Y.). At the end of the study cells were washed twice with ice cold phosphate buffered saline, pH 7.5 (PBS). One ml of media from each flask was removed after treatment and stored at −80° C. for measurement of VEGF levels.

Cell growth and viability assays. Growth inhibition assays were carried out using the 3-[4,5-dimethylthiazol-2-yl]-2,5-diphenyltetrazolium bromide (MTT) assay. For analysis under hypoxic conditions, plates were incubated for 16 h in 1% oxygen in the presence of the drug then placed in 20% oxygen for the remainder of the 72 h.

Immunoblotting. Nuclear and cytoplasmic extracts were prepared using NE-PER™ Nuclear and Cytoplasmic Extraction Reagents according to the manufacturer's instructions. Western blotting was performed using mouse anti-human HIF-1α (1 μg/ml); mouse anti-human HIF-1β (1 μg/ml); mouse anti-human iNOS (5 μg/ml); and goat anti-human lamin A (0.5 μg/ml). Anti-mouse or anti-goat horseradish peroxidase-conjugated secondary antibodies were used at a dilution of 1:5000 for detection by chemiluminescence and blots were quantified using ImageQuant software.

Immunohistochemistry. Human breast carcinoma MCF-7 cells ($10^7$ cells in matrigel per mouse) were injected subcutaneously into the flanks of SCID mice implanted with estrogen pellets. Tumors were allowed to grow to 0.5 g. The mice then received intraperitoneal vehicle alone or 120 mg/kg PX478. Four hours later the tumors were excised, fixed in formalin and embedded in paraffin. Sections were stained with antibodies to HIF-1α (10 μg/ml; Transduction Labs) or VEGF (7 μg/ml) using an automated immunostainer system. Staining was quantified using Simple PCI analysis software.

PX-478 shows inhibition in hypoxia and normoxia. Human breast carcinoma and human colon carcinoma HT-29 cells were treated for 16 hr with varying concentrations of PX-478 in the presence of normoxia (20% oxygen) or hypoxia (1% oxygen). The cells were then washed three times with warm drug-free medium and incubated for the remainder of 72 hr. The MTT assay was then carried out to determine growth inhibition. Data in Table 1 represent the mean±SE from three experiments carried out in duplicate. PX-478 shows growth inhibition under hypoxia (1% oxygen) and normoxia (20% oxygen) (p=<0.01) with a ratio of growth inhibition under hypoxia to that in normoxia at 1.25 in MCF-7 cells and 1.20 in HT-29 cells.

TABLE 1

| CELL LINE | $IC_{50}$ (μM) | |
| --- | --- | --- |
|  | Normoxia | Hypoxia |
| MCF-7 | 25.1 ± 1.5 | 20.0 ± 2.0 |
| HT-29 | 29.5 ± 2.4 | 23.9 ± 2.3 |

PX-478 inhibits HIF-1α protein. HIF-1α is a key controller of the cellular response to hypoxia. Therefore, we examined the effect of PX-478 on HIF-1α protein levels. As shown in FIG. 1, PX-478 inhibits hypoxia-induced (1% oxygen) HIF-1α protein in human breast carcinoma MCF-7 (FIG. 1A) and human colon carcinoma HT-29 cells (FIG. 1B), with $IC_{50}$ values of 3.5±2.0 and 17.8±5 μM respectively. HIF-1α protein levels were very low under normoxia (20% oxygen) as reported previously so no effect was seen. No effect of PX-478 was seen on HIF-1β levels (FIGS. 1A and 1B).

EXAMPLE 2

Figure 2:
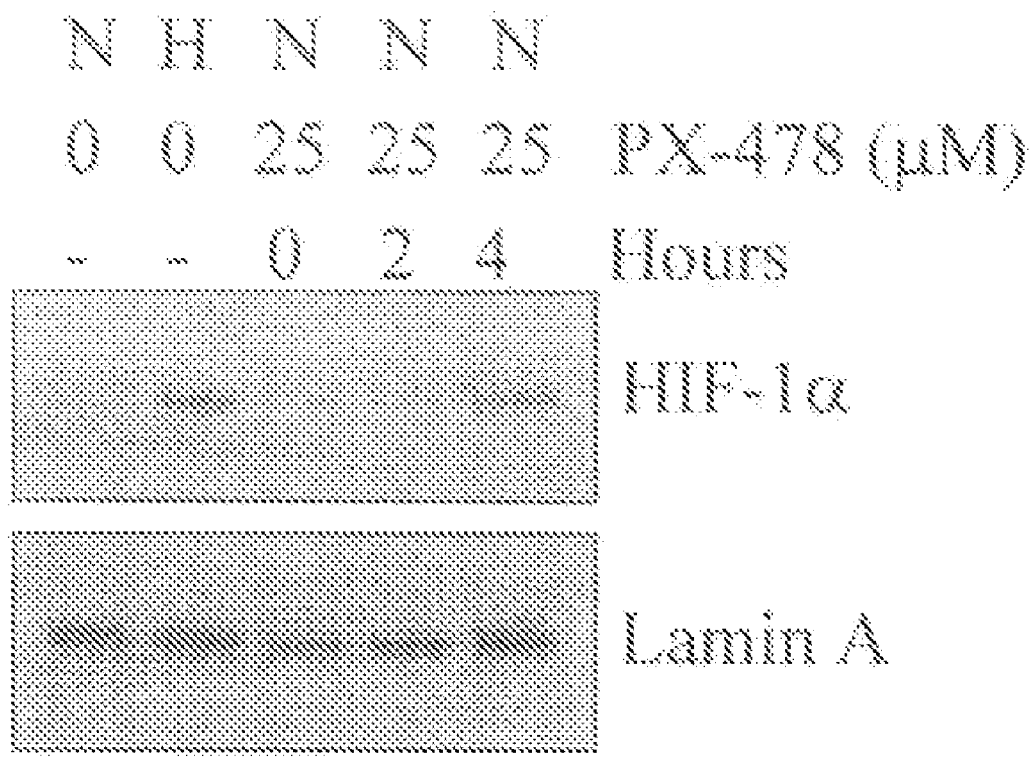
FIG. 2 illustrates the recovery of HIF-1α protein after inhibition by PX-478.

HIF-1α protein remains inhibited for up to 4 h after removal of PX478. To investigate how long HIF-1α protein remains inhibited after treatment of cells with PX-478, MCF-7 cells, as shown in FIG. 2, were treated with PX-478 25 μM for 16 h, the drug was then washed out and recovery of HIF-1α was measured. Nuclear cell extracts were prepared at the time points indicated and Western blotting was performed to measure levels of HIF-1α protein. Levels of HIF-1α protein after 16 h under normoxia (20% oxygen; N) are also shown as a control. HIF-1α protein levels returned to pre-treatment levels within 4 h of removal of the drug.

EXAMPLE 3

Figure 3:
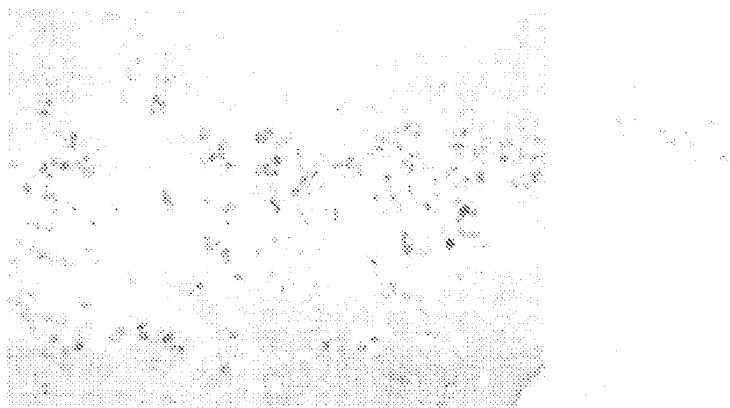
FIGS. 3A, 3B, and 3C illustrate the effect of PX-478 on HIF-1 in vivo.
Figure 3:
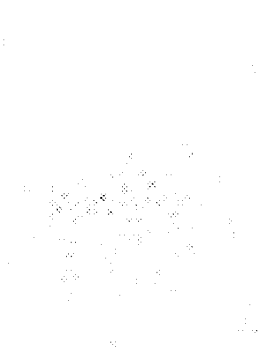
Figure 3C:
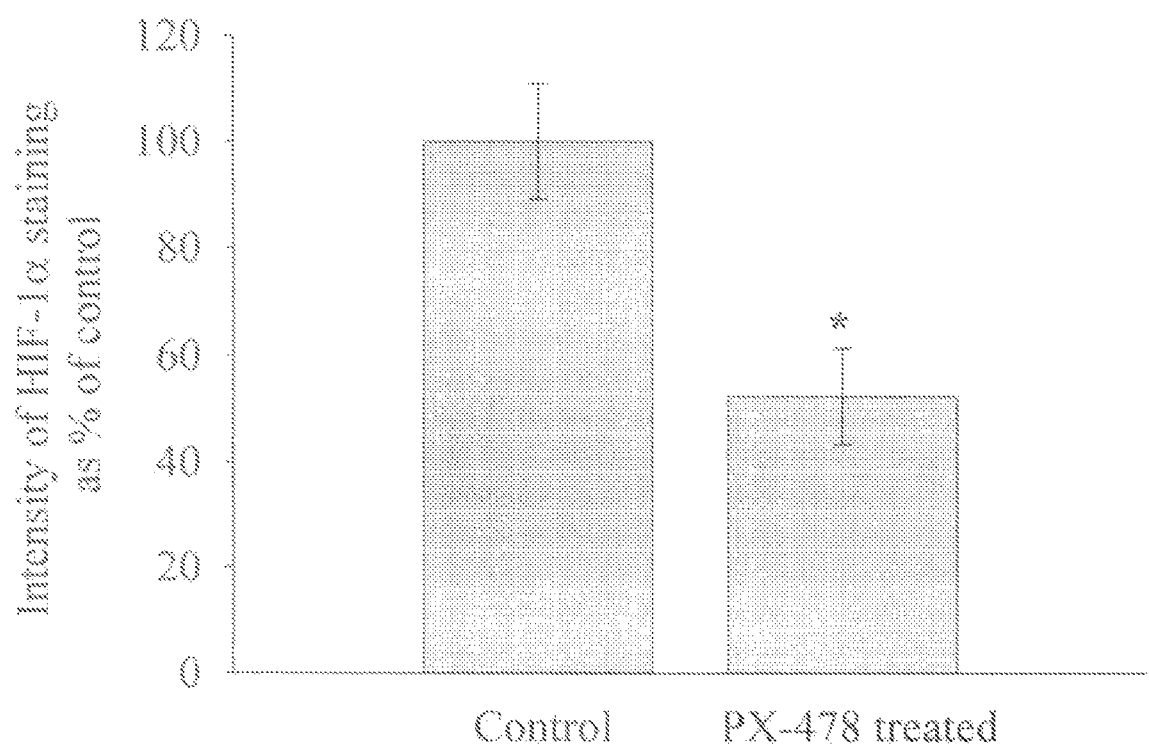

PX-478 inhibits HIF-1α protein in vivo. MCF-7 cells were grown as xenografts in the flanks of SCID mice. When the xenografts reached 0.3 g the mice were treated with vehicle control or 100 mg/kg PX-478 (FIGS. 3A and 3B respectively). Four hours later tumors were removed, formalin fixed, embedded in paraffin and the level of HIF-1α protein was measured using immunohistochemistry (FIGS. 3A and 3B). In FIG. 3C, the intensity of HIF-1α staining was quantified using Simple PCI software. The asterisk (*) shows a significant difference from controls (p=<0.01). Data represent the mean±SE. As shown in FIGS. 3A and 3B, treatment of MCF-7 cells grown as xenografts in the flanks of SCID mice showed significantly decreased levels of HIF-1α protein after 4 hr treatment with PX-478 (p=<0.005). Staining remained nuclear in localization even in PX-478 treated cells but levels of HIF-1α were decreased to 50% in PX-478 treated mice compared to untreated controls as shown in FIG. 3C.

Recently, several drugs have been reported to indirectly inhibit the HIF-1 complex. As mentioned above, the HSP90 inhibitor geldanamycin has been reported to inhibit HIF-1α protein by a pVHL-independent mechanism. A number of camptothecin analogues have also been identified as inhibitors of HIF-1α protein and transactivation using a high-throughput screening approach. It is not clear if these compounds simply inhibit general transcription via topoisomerase I inhibition or act as specific HIF-1 inhibitors. DX-2-1 (a carbomycin derivitive) was also identified using the same screen but is known to affect a number of transcription factors in addition to HIF-1. We have previously identified two inhibitors of the thioredoxin-1 redox system, PX-12 and pleurotin, as inhibitors of HIF-1α protein, HIF-1 transactivation and hypoxia-induced VEGF production in vitro and HIF-1α protein in vivo. Treatment methods using any HIF inhibitor, including any of the drugs discussed herein, would benefit from the present invention to help determine a physiologically effective dose and to select patients that will most benefit from treatment.

The effect of PX-478 against Panc-1 human pancreatic cancer as MCF-7 Human Breast Cancer; Human Prostate Cancer and HT-29 Colon Cancer were previously shown in U.S. Ser. No. 10/929,156, filed Aug. 30, 2004, the entirety of which is hereby incorporated by reference. The effect of PX-478 on HT-29 Tumor xenograph HIF-1α and on plasma VEGF levels were also shown in U.S. Ser. No. 10/929,156.

EXAMPLE 4

Jurkat and PBMC Activation and DFO Treatment Protocol for HIF-1α Induction

Hypoxia induction: PBMC. Peripheral Blood Mononuclear Cells (PBMCs) were isolated from heparinized blood of healthy volunteers using Histopaque-1077 (Sigma-Aldrich) density gradient centrifugation. To induce leukocyte activation, PBMC were incubated overnight in AIMV media supplemented with 5% FCS, 5 ng/mL IL-15, 100 U/mL IL-2 (Peprotech, Rocky Hill, N.J.) in the presence or absence of 1 or 50 ng/mL phorbol myristate acetate (PMA) (EMD Biosciences, La Jolla, Calif.) and 250 ng/mL calcium ionophore A23187 (Sigma). To simulate hypoxia, 50 μM DFO was added for 16 hr. The PBMCs were then harvested and analyzed by flow cytometry or Western for HIP-1α protein expression.

Western Blot: Standard Western blot procedures were used to analyze nuclear extracts (10 μg/lane) on a 12% gel, transferred to PVDF membrane and immunoblotted with 1 μg/mL rabbit polyclonal anti-HIF-1α antibody H-206 (Santa Cruz Biotechnology, Santa Cruz, Calif.) and developed with SuperSignal® West Dura Extended Duration Substrate kit (Pierce). The immunocomplexes were visualized on a Kodak Image Station 440 CF (Eastman Kodak Company, Rochester, N.Y.).

Figure 4:
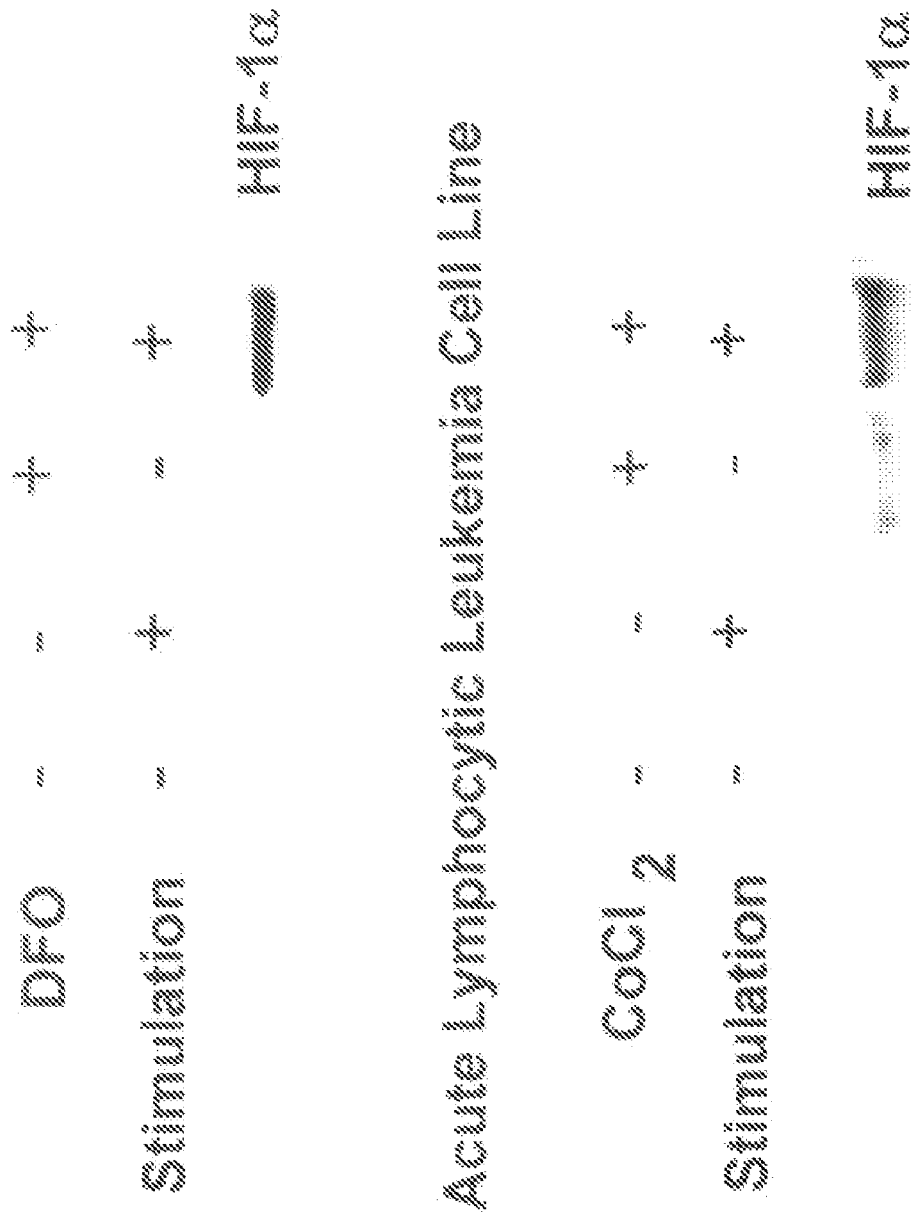
FIG. 4 illustrates DFO and $CoCl_2$ can induce HIF-1α upregulation in normal leukocytes (PBMC) and leukemic T cells (Jurkat)

Results. Upregulation of HIF-1α in primary stimulated PBMC or the acute leukemia tumor cell line Jurkat, can be induced in vitro using deferoxamine (DFO), an iron chelator or Cobalt chloride ($CoCl_2$). PBMC were left unstimulated or were stimulated with PMA (50 ng/mL) and the calcium ionophore A23187 (250 ng/mL) for 16 hours in the presence or absence of the iron chelator DFO (10 μM) to mimic the effects of hypoxia. Jurkat tumor cells were left unstimulated or were stimulated with PMA (50 ng/mL) and the calcium ionophore A23187 (250 ng/mL) for 16 hours in the presence or absence of $CoCl_2$ (100 μM) to mimic the effects of hypoxia. The cultured PBMC or Jurkat cells' HIF-1α protein levels were assessed in 5 μg of nuclear extracts by Western blot. (FIG. 4).

Figure 5A:
FIGS. 5A and 5B illustrate PX-478 exposure decreases HIF-1α expression in stimulated/hypoxic PBMC and Jurkat cells and can inhibit hypoxia induced accumulation of the HIF-1α protein.
Figure 5A:
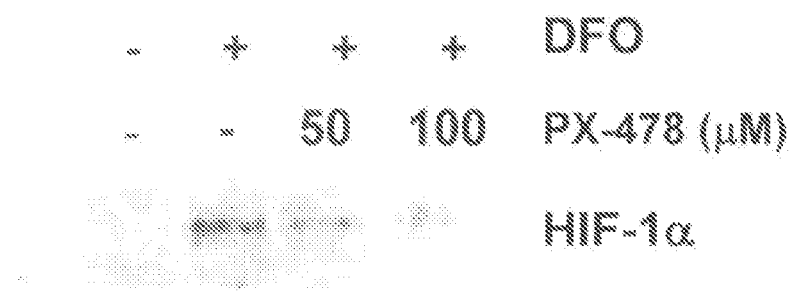

Stimulation with PMA and Ionophore increased the levels of HIF-1α expression seen in both primary leukocytes and tumor cells. PX-478 reduced the HIF-1α expression in both the cell line and freshly isolated PBMC in a dose and time dependent manner. Freshly isolated PBMC were incubated for 16 hours in the presence of 10 μM DFO, and stimulated with PMA (50 ng/mL) and Ionophore (A23187; 250 ng/mL) in RPMI supplemented with 10% FCS, 50 U/mL IL-2, and 5 ng/mL IL-15. PX-478 was added at 50 or 100 μM for an additional 4 hours before 5 μg of nuclear extracts were analyzed HIF-1α protein expression by Western Blot. Jurkat cells were incubated with DFO (10 μM) for 16 hours before the addition of either 50 or 100 μM PX-478. After 4-hour incubation, 5 μg of nuclear extracts were analyzed HIF-1α protein expression by Western Blot. Reduction in HIF-1α expression levels was seen within 4 hours at high concentration (50-100 μM) PX-478 (FIG. 5A).

Figure 5B:
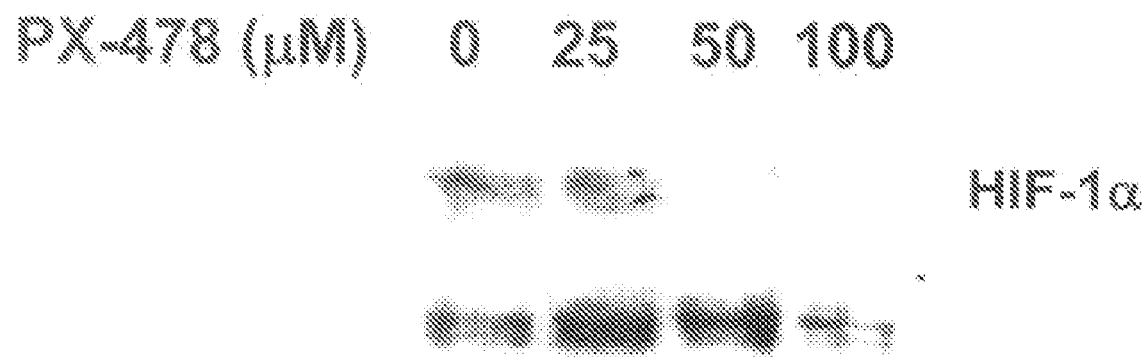

To test detection of PX-478 inhibition of HIF-1α upregulation, the CD4+ T cell tumor cell line Jurkat was pre-treated with varying doses of PX-478 for 30 minutes prior to exposure to DFO for 4 hours to induce HIF expression. The cells were then harvested, lysed and the nuclear extracts were analyzed by Western blot for HIF-1α protein expression (FIG. 5B). At a concentration of 50 µM, PX-478 was able completely inhibit HIF accumulation in the Jurkat cells. According to one aspect of the invention, therefore, PX-478 treated patients can likewise be monitored for the ability of an HIF inhibitor to inhibit the upregulation of an HIF, e.g., HIF-1α. In lieu of doing an invasive procedure to procure tumor biopsy specimens before and after PX-478 treatment, PBMC can be used as a surrogate biomarker to determine if the PX-478 blood levels are high enough to inhibit HIF-1α upregulation in the presence of hypoxia mimicking chemicals such as DFO or $CoCl_2$.

EXAMPLE 5

Development of Flow Cytometric Based Assay for Detection of HIF-1α in PBMC and Leukemic Cell Lines.

Intracellular Staining of Peripheral Blood Mononuclear Cells (PBMC) and a Jurkat Leukemia Cell Line. Western blot analysis of HIF-1α requires large numbers of cells and is time consuming. These attributes makes it impractical as a method to screen or follow patients being treated by HIF-1α inhibitors in the clinic. Therefore, we developed a flow cytometric assay that could be used to quantitate HIF-1α upregulation and/or inhibition in leukemic cells or peripheral blood mononuclear cells. This assay provides more rapid analysis of clinical samples requiring far fewer cells than the standard Western blot procedure.

Cells were fixed with 1.5% formaldehyde for ten minutes, permeabilized with ice cold methanol for 20 minutes, and stained with 1.7 µg/mL of the mouse monoclonal anti-HIF-1α antibody (BD Bioscience, San Diego, Calif.) or 1 µg/mL rabbit polyclonal anti-HIF-1β (Arnt 1) antibody (Santa Cruz Biotechnology, Santa Cruz, Calif.) for 30 minutes at 4° C. The cells were washed and stained with the secondary (3.75 µg/mL final concentration) FITC-conjugated $F(ab')_2$ goat anti-mouse IgG antibody (Jackson ImmunoResearch, West Grove, Pa.) or a 1:3000 dilution of AlexaFluor-conjugated anti-Rabbit IgG (gift from Garth Powis). After 25 minute incubation at 4° C. in the dark, the cells were washed, resuspended in 1% formaldehyde in PBS and analyzed for protein content within 24 hours on a FACScan flow cytometer (BD Biosciences, San Jose, Calif.).

Figure 6A:
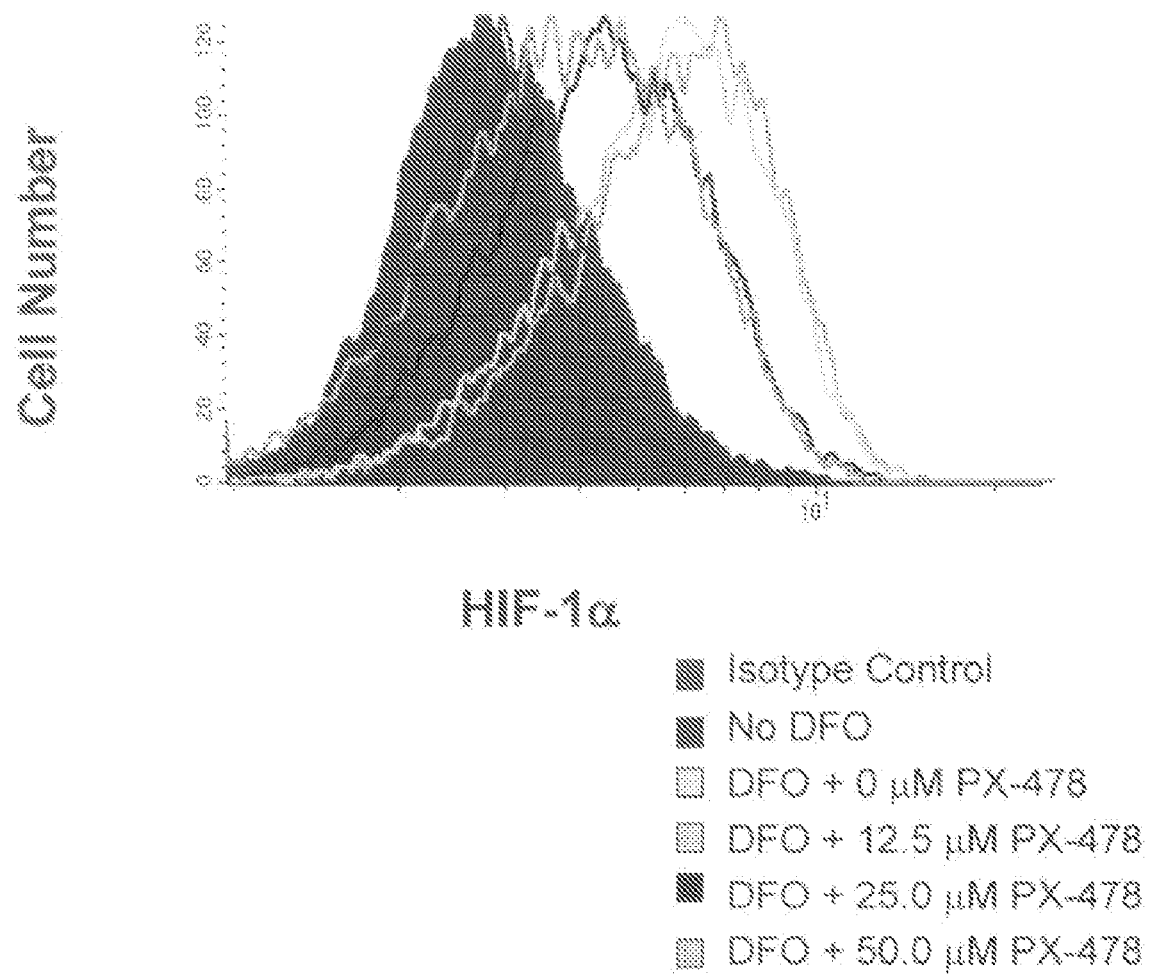
FIGS. 6A and 6B illustrate HIF-1α upregulation and inhibition by PX478 can be quantified by flow cytometry.
Figure 6B:
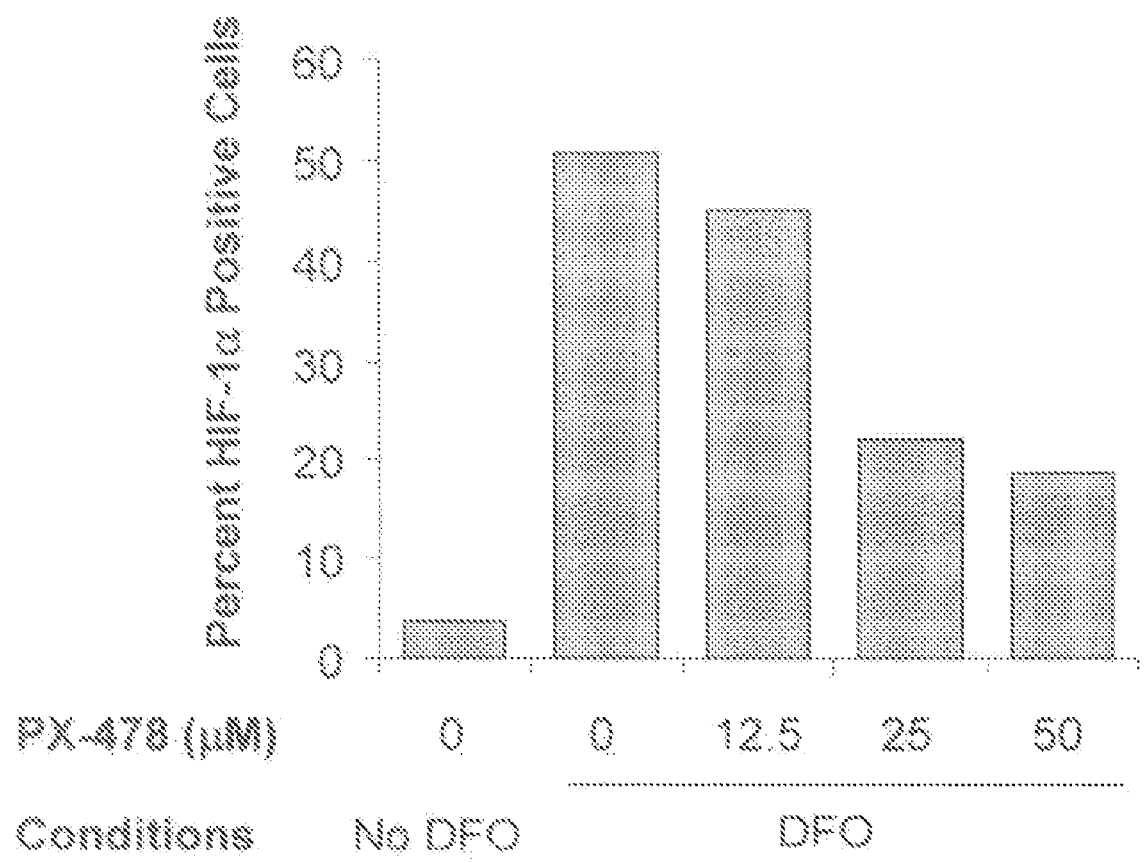

As shown in FIG. 6A, HIF-1α expression of Jurkat cells under normoxia (purple filled histogram, no DFO exposure) was compared to cells grown in DFO-mediated hypoxia (open histograms) in the presence or absence of the HIF-α inhibitor, PX478. After a 5 hour exposure to DFO (50 µM), PX478 was added at 0 (green line), 12.5 (blue line), 25 (black line), or 50 µM (orange line) final concentrations for a further 16 hour incubation before the cells were harvested and analyzed for HIF-1α expression by flow cytometry. Background staining is shown for non-specific mouse IgG control antibody (red line). FIG. 6B gives a graphic representation of the percent of cells with HIF-1α staining over Isotype control for each condition. The results show that after 16 hour incubation with 25 µM of the HIF-1α inhibitor PX478, a 50% reduction was seen in the HIF-1α protein expression in Jurkat tumor cells.

Figure 7A:
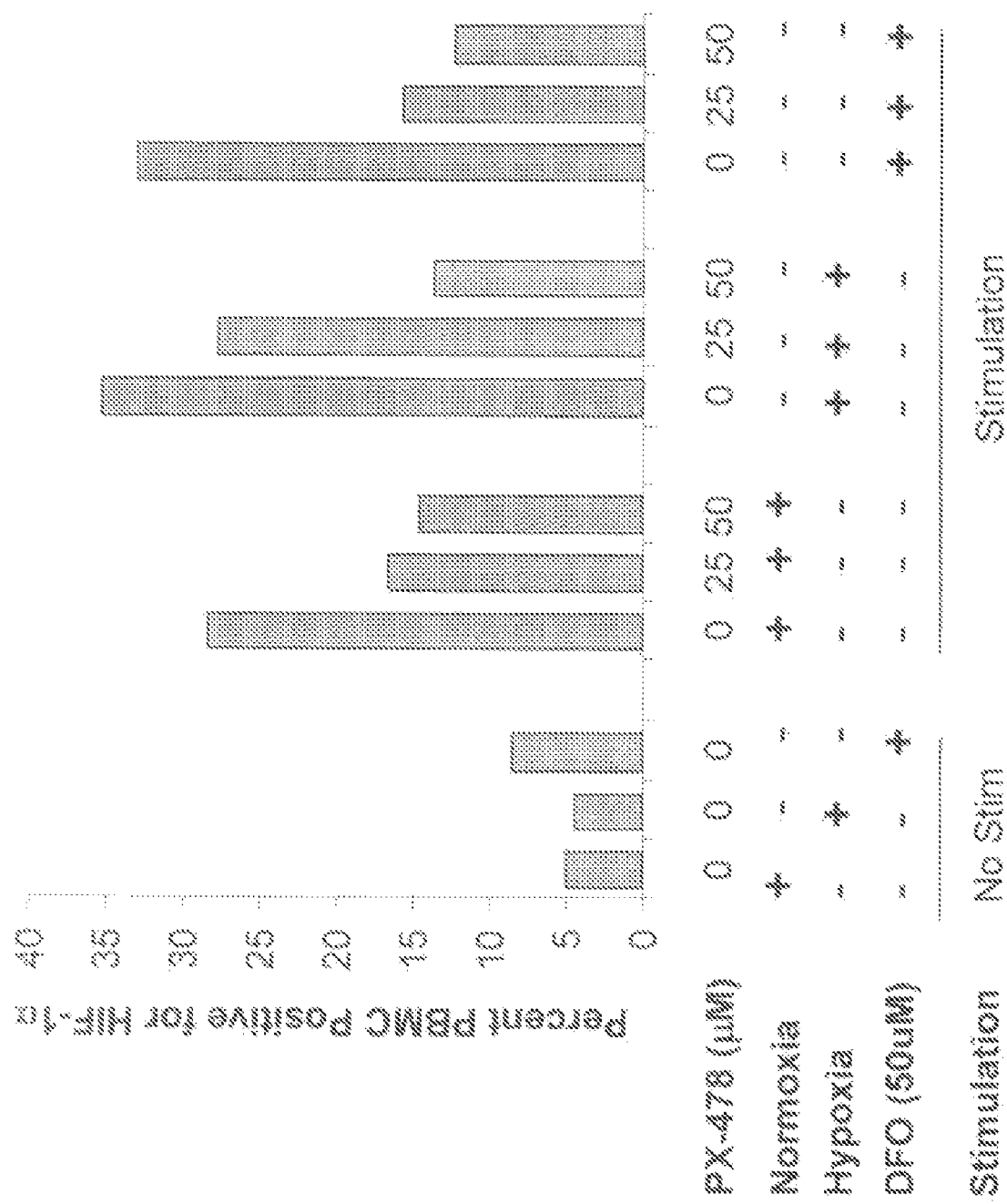
FIGS. 7A and 7B illustrate HIF-1α but not HIF-1β is down regulated by PX478 in freshly isolated PBMC as measured by flow cytometry.
Figure 7B:
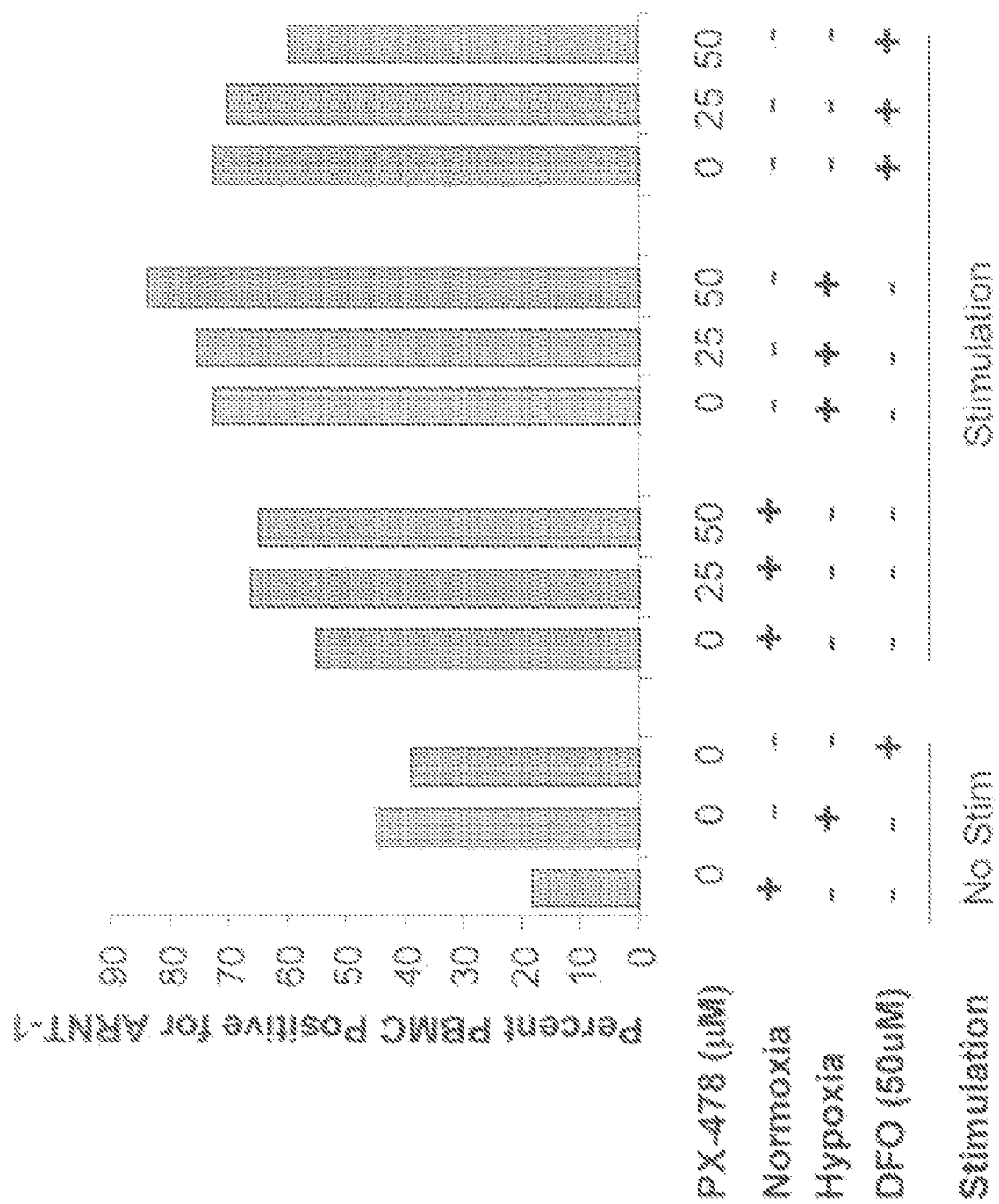
Figure 8A:
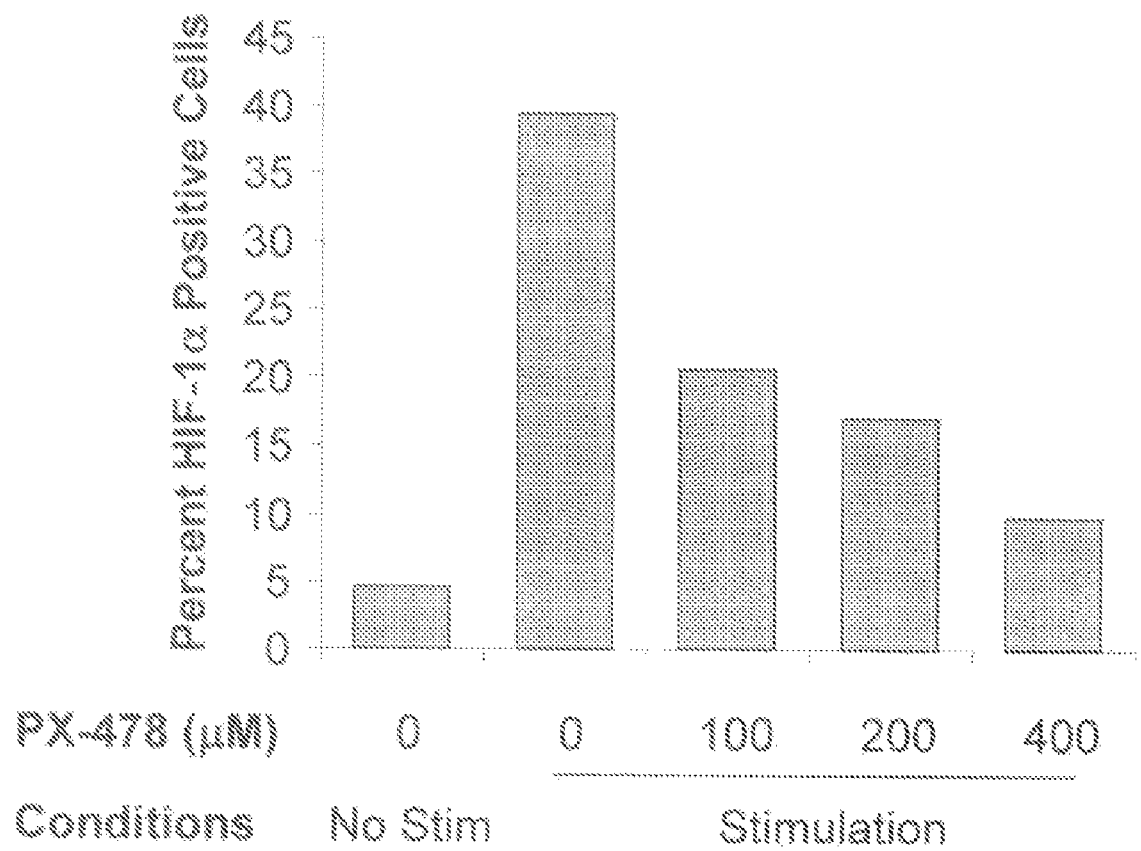
FIGS. 8A and 8B illustrate a rapid and dose dependent decrease in HIF-1α due to PX478 spiked into human whole blood.
Figure 8B:
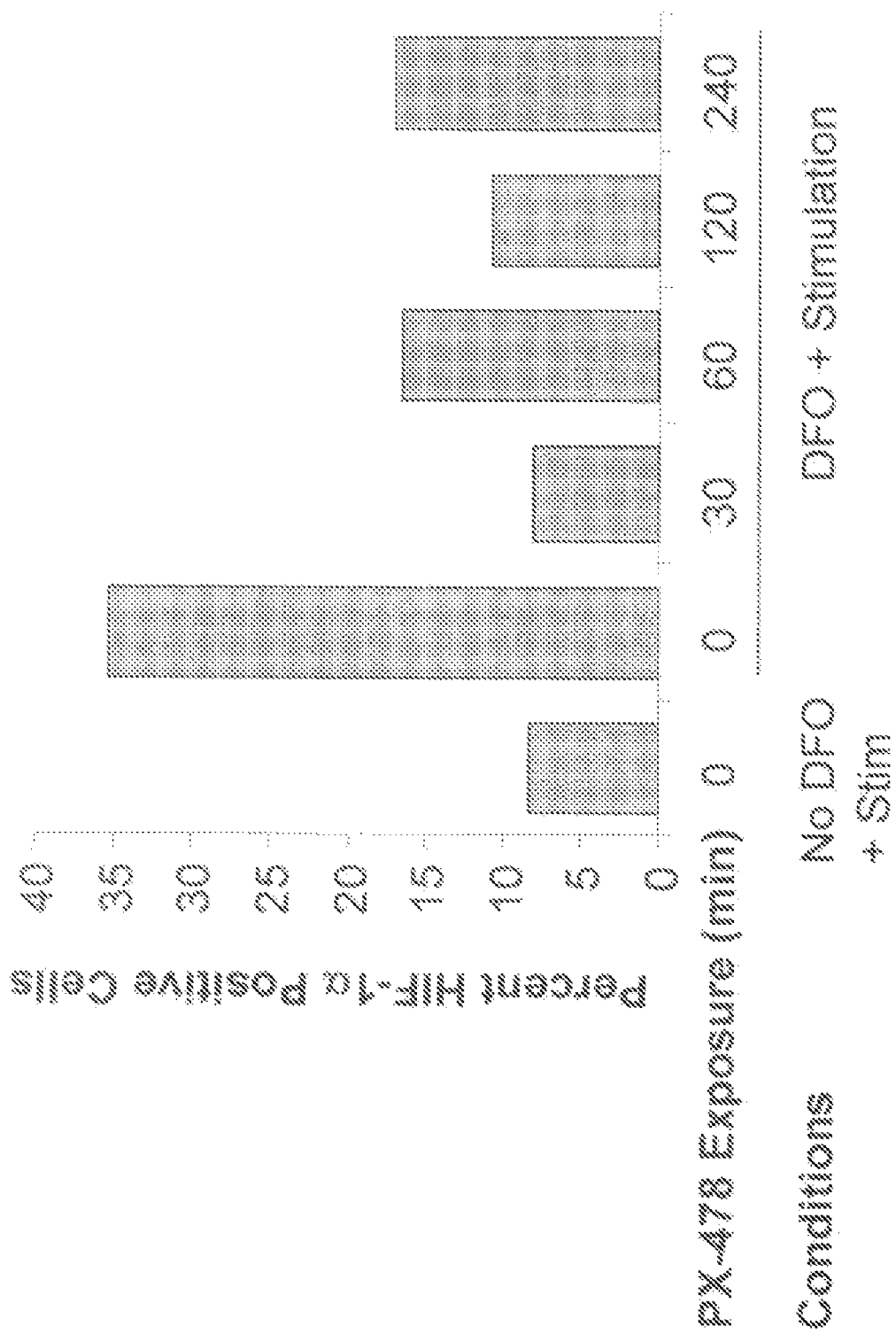

The flow cytometric assay was able to detect the HIF-1α upregulation of HIF-1α due to true hypoxia (1% $O_2$), DFO mediated hypoxia (50 µM DFO) or to stimulation alone in PBMC isolated from a normal donor compared to cells incubated in normoxia (20% $O_2$). The subsequent block of HIF-1α upregulation after a 16 hour exposure to 25 or 50 µM PX-478 under all three conditions is shown in FIG. 7A. We were also able to show that the constitutively expressed HIF-1β protein levels were not significantly impacted by the HIF-1α inhibitor PX478 by staining for HIF-1β protein as described in the methods above. (FIG. 7B). The present invention is useful in determining the expression between HIF-1α expression and other proteins of interest that may or may not be the intended target of the drug being tested.

a particularly useful aspect of the present invention is the ability to monitor the effective dose of drug needed to inhibit HIF expression or activity in individual patients. To demonstrate that the assay can be used to monitor a difference in HIF-1α expression before and after treatment in a dose dependent manner, we spiked whole blood from a normal donor with increasing concentrations of PX-478. After a two hour incubation, the PBMC were isolated as described above by density gradient centrifugation and after extensive washing were incubated in the presence of stimulatory PMA and Ionophore for 16 hours. The resulting cells were then fixed, permeabilized and stained as described in the methods section. The flow cytometric analysis is depicted in FIG. 8A. After only a two hour exposure to PX-478, there was a significant inhibition of HIF-1α upregulation by the lymphocytes. A time course showed that even a 30 minute exposure of whole blood to 100 µM PX478 gave maximal blocking of HIF-1α upregulation (FIG. 8B).

The current study explored the use of HIF-1α upregulation in peripheral mononuclear blood cells as a means to follow HIF-1α inhibition by PX-478 in a clinical setting. It is known that HIF-1α plays a critical role in the survival and function of activated lymphocytes and has been found to be strongly expressed in highly proliferative acute lymphocytic leukemias. Upregulation of HIF-1α protein expression in freshly isolated peripheral blood mononuclear cells (PBMC) and the Jurkat acute leukemia tumor cell line, in vitro was accomplished using deferoxamine (DFO), an iron chelator, or $CoCl_2$ in combination with phorbol-12-myristate-13-acetate (1 or 50 ng/ml) and ionophore A23187 (250 ng/ml) for 16-24 hours under normoxia. This treatment produced a similar upregulation of HIF-1α as 1% oxygen exposure. It was found that the HIF-1α inhibitor, PX-478 reduced the HIF-1α expression in both the cultured cell line and freshly isolated PBMC to background levels within 4 hours in a dose response fashion. HIF-1β is not affected by PX-478. Flow cytometry can be used to measure HIF-1α induction and inhibition by HIF-1α inhibitors, as well as measure levels of other proteins such as HIF-1β. PBMCs from freshly isolated whole blood exposed to PX-478 showed HIF-1α inhibition, as measured by flow cytometry. Flow cytometry to monitor HIF-1α in PBMCs during PX-478 drug treatment of cancer patients, therefore, can provide a surrogate biomarker assay for clinical efficacy.

EXAMPLE 6

Identifying Subjects that Will Respond to HIF-1α Inhibitors.

PBMC Isolation and Stimulation. Peripheral Blood Mononuclear Cells (PBMC) were isolated from heparinized blood of healthy volunteers or advanced cancer patients using Histopaque-1077 (Sigma-Aldrich) density gradient centrifugation. The PBMC were washed in PBS three times at low speed (200×g) to remove contaminating platelets. The resulting PBMC were incubated overnight at $2-4\times10^6$ cells/mL in 1 mL AIM-V medium (Invitrogen, Carlsbad, Calif.) supplemented with 5% FCS, 5 ng/mL IL-15 and 100 U/mL IL-2 (Peprotech, Rocky Hill, N.J.) in 48 well tissue culture plates. Leukocyte activation was induced with 1 ng/mL phorbol myristate acetate (PMA)(EMD Biosciences, La Jolla, Calif.) and 250 ng/mL calcium ionophore A23187 (Sigma) and 50 µM deferoxamine (DFO) was used to simulate hypoxia. After 16 hour incubation at 37° C. in 5.5% $CO_2$, the cells were harvested for HIF-1α protein analysis by flow cytometry or Western Blot.

Intracellular and Extracellular Staining of Peripheral Blood Mononuclear Cells (PBMC). Cells were fixed by adding 81 μL of 37% formaldehyde to 2 mL of harvested cells for a final concentration of 1.5% formaldehyde and incubated for ten minutes at room temperature. The cells were spun down and the pelleted cells were permeabilized by adding 500 μL ice cold 100% methanol dropwise while vortexing, then incubating on ice for 20 minutes. The cells were washed twice with 1 mL FACS Buffer (PBS+1% BSA) and stained with 1.7 μg/mL of the mouse monoclonal anti-HIF-1α antibody (BD Biosciences, San Diego, Calif.) in 100 μL FACS Buffer for 30 minutes at 25° C. The cells were washed twice with 2 mL FACS Buffer before staining with the secondary (3.75 μg/mL final concentration) FITC-conjugated F(ab')2 goat anti-mouse IgG antibody (Jackson ImmunoResearch, West Grove, Pa.) for 25 minutes at 4° C. in the dark. For samples requiring extracellular staining the cells were washed extensively (three times with 2 mL FACS Buffer) after HIF-1α staining, then incubated for 20 minutes at 4° C. with 5 μl of anti-CD3-PE-Cy5 (BD Biosciences) and anti-CD19-PE antibody (BioLegend, San Diego, Calif.) in a 100 μl FACS Buffer. The cells were then washed and resuspended in 200 μL of 1% formaldehyde in FACS Buffer for analysis within 24 hours on a FACScan flow cytometer (BD Biosciences, San Jose, Calif.).

Figure 9:
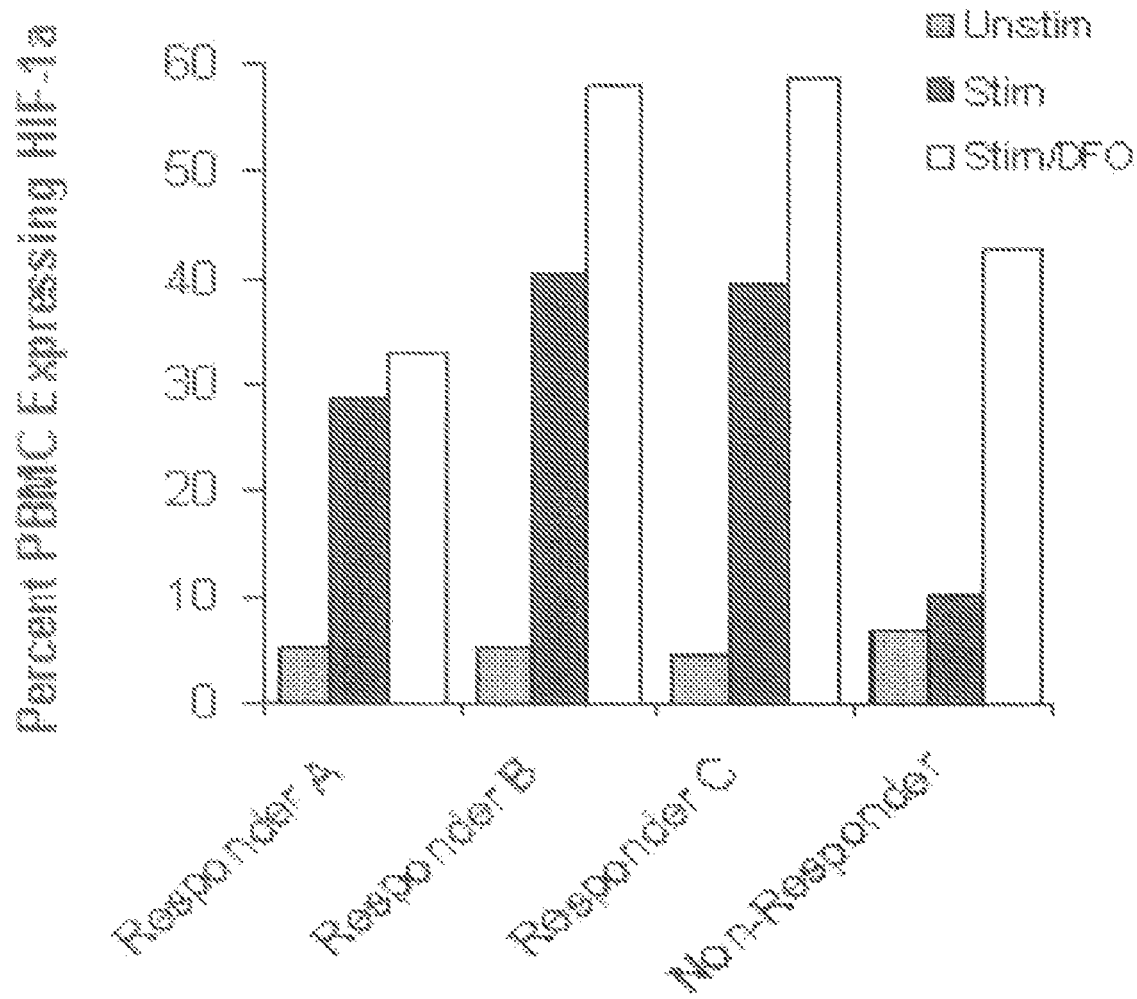
FIG. 9 illustrates stimulation of whole blood with PMA and ionophore alone in responders and a non-responder, as measured by flow cytometry.
Figure 10:
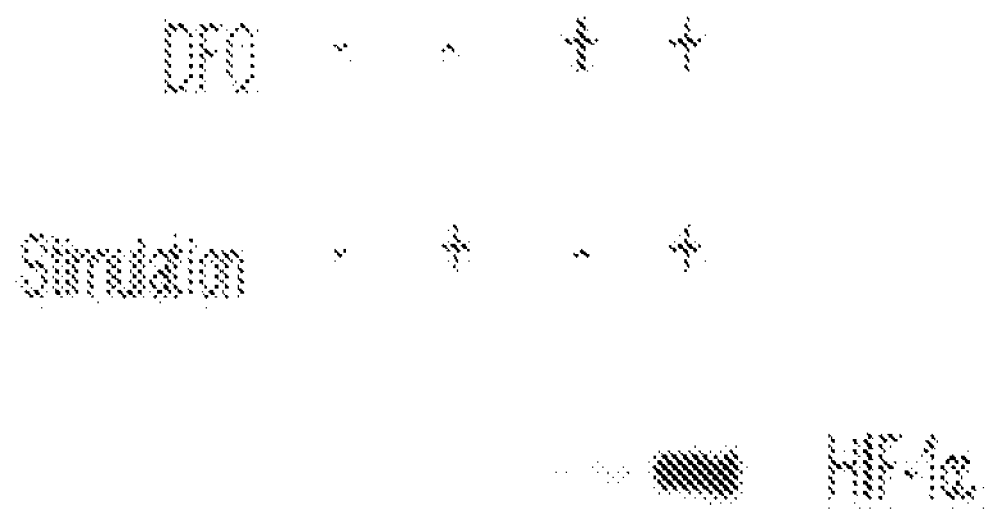
FIG. 10 illustrates stimulation of PBMCs with PMA and ionophore alone in a non-responder, as measured by Western analysis.

As shown in FIG. 9, HIF-1α accumulation in PBMCs was seen when the cells were stimulated and could typically be enhanced under hypoxia (responder). However, it was found that donors whose PBMCs did not upregulate HIF-1α upon stimulation alone required a second signal such as hypoxia to visualize this protein's accumulation by flow cytometry (FIG. 9; non-responder). The absence of HIF-1α accumulation with PMA/ionophore stimulation alone in the non-responder was confirmed by Western Blot (FIG. 10).

Figure 11:
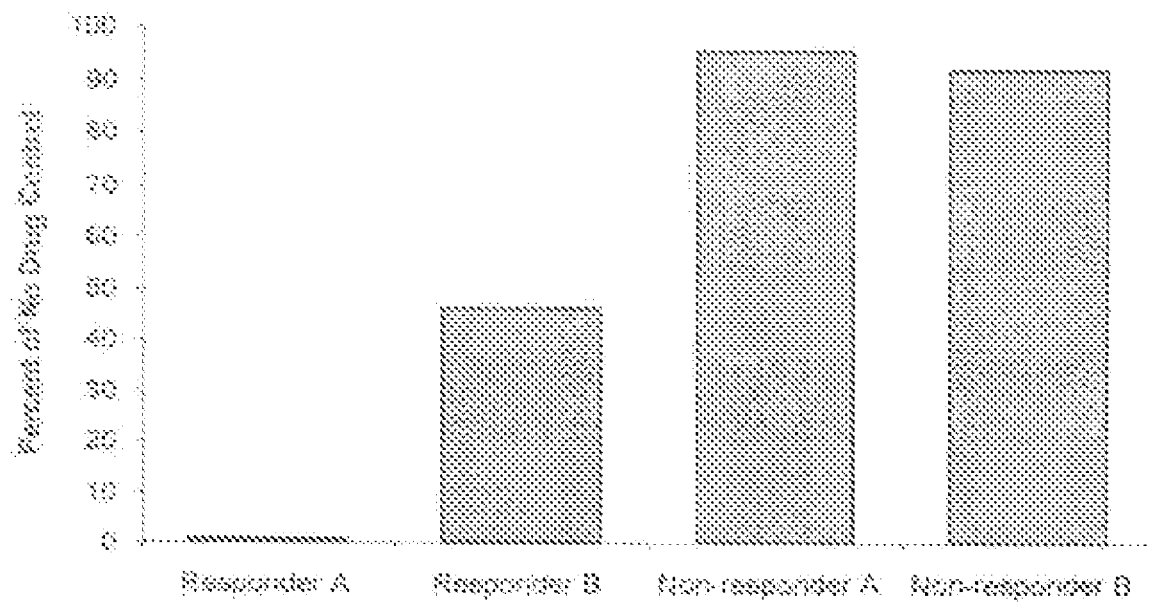
FIG. 11 illustrates treatment of stimulated responder and non-responder PBMCs with PX478.

PX-478 added directly to whole blood of two non-responders for 1 hour before the isolation of PBMCs and subsequent stimulation with PMA/ionophore and DFO had no effect on the HIF-1α levels under the same conditions that lowered the HIF-1α expression of two other normal donors by at least about 50% (FIG. 11). Whole blood was isolated from normal donors that upregulate HIF-1α upon stimulation with PMA/Ionophore alone (responders) or that require hypoxia in addition to PMA/Ionophore stimulation (non-responders) in order to upregulate HIF-1α expression. The whole blood was spiked with PX-478 (100 μM) for 1 hour at 37° C. before PBMCs were isolated by density gradient centrifugation, washed extensively, and incubated with PMA/ionophore and DFO (50 μM) (responder A, and non-responders A & B) or with PMA/ionophore alone (responder B) overnight. The resulting PBMCs were harvested, fixed, permeablilized and stained for HIF-1α expression either in the live lymphocyte gate (responder A & B and non-responder A), or in the CD3+ T cell subset (non-responder B). The cells were analyzed by flow cytometry for the percent gated cells expressing HIF-1α.

EXAMPLE 7

Feasibility of Using Flow Cytometric Assay to Detect HIF-1α Regulation in Advanced Cancer Patients.

Figure 12A:
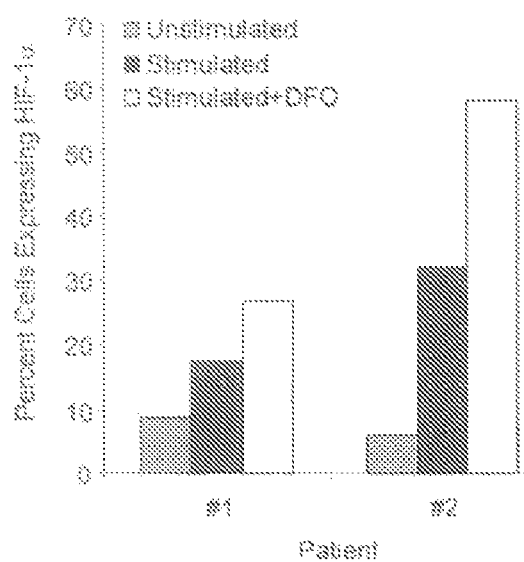
FIGS. 12A and 12B illustrate HIF-1α expression in stimulated and unstimulated cancer patient total lymphocyte population and in the T cell and B cell subsets.
Figure 12B:
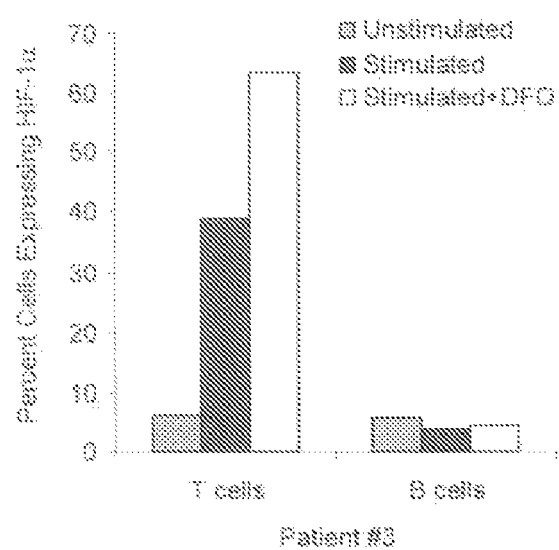

Developing anti-cancer drugs requires working with a unique patient population that typically has undergone multiple courses of chemotherapy and has decreased white cell counts. Therefore, the feasibility of using the flow cytometric HIF-1α assay as a surrogate marker in a clinical trial setting was tested in three separate advanced cancer patients. Peripheral blood (18 mL) from two patients with advanced gastrointestinal cancer was used to isolate PBMCs. As described above, PBMCs from 2 ten mL heparin coated tubes were isolated by the standard density gradient method, cryopreserved, and stored in liquid nitrogen. The cells were thawed on the day of the assay, washed, then stimulated with PMA (1 ng/mL) and ionophore (250 ng/mL) with or without DFO (50 μM) for 16 hours (at 37° C., 5.5% $CO_2$) in AIMV media containing 5% FCS, 100 U/mL IL-2 and 5 ng/mL IL-15. The cells were then harvested, fixed, permeabilized, and stained for HIF-1α expression in the total gated lymphocyte population (FIG. 12A). Cells in the live lymphocyte gate were analyzed on the FACScan flow cytometer for percent cells expressing the HIF-1α protein. Peripheral blood mononuclear cells from a third cancer patient was incubated for 16 hours with or without stimulation (1 ng/mL PMA and 250 ng/mL Ionophore) and DFO (50 μM) at 37° C. in 5.5% CO2 (FIG. 12B). The cells were then harvested, fixed, permeabilized and stained for HIF-1α CD3 and CD19. The cells then underwent 3-color analysis on the FACScan flow cytometer to determine the percent of gated CD3+ T cells and CD19+ B cells that express HIF-1α. To analyze HIF-1α expression in either the T cell or B cell subpopulations, the HIF-1α stained PBMC were also labeled with anti-CD3 (T cells) and anti-CD19 (B cells). Each subpopulation was analyzed separately for HIF-1α expression using 3-color analysis on the FACScan flow cytometer (FIG. 12B).

Our results indicate that it is possible to detect HIF-1α upregulation in an advanced cancer patient's PBMCs. In order to enhance HIF-1α detection and to better determine the effects the drug has on the protein's upregulation, gating specifically on the CD3 positive T cells provides cleaner and more sensitive data.

Figure 13A:
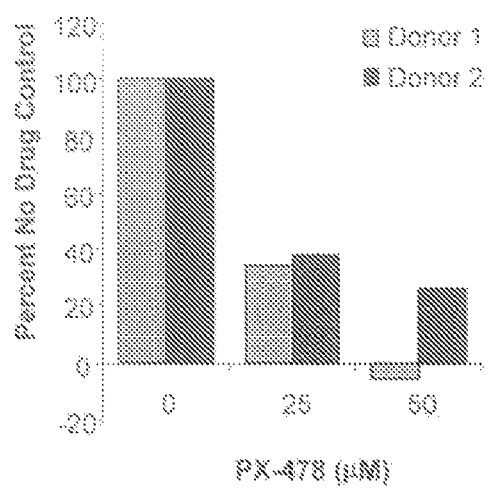
FIGS. 13A and 13B illustrate HIF-1α expression in normal donors' stimulated PBMCs treated with two different HIF-1α inhibitors.
Figure 13B:
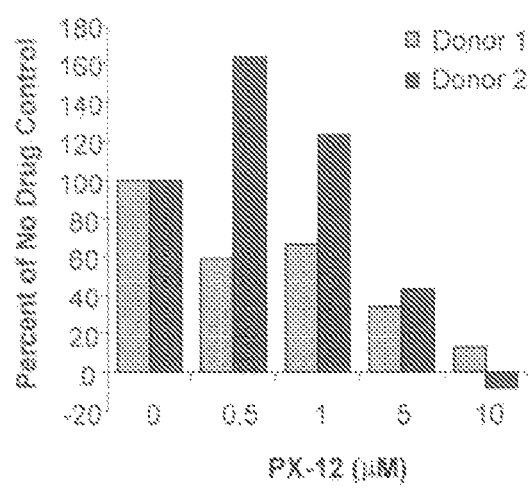

Analyzing HIF-1α suppression can be a useful biomarker for any drug that directly or indirectly target HIF-1α protein expression. PBMCs isolated from two normal donors were stimulated with PMA (1 ng/mL) and ionophore (250 ng/mL) in the presence of DFO (50 μM) as described earlier and incubated for 16 hours with or without 25 or 50 μM PX-478 that targets HIF-1α expression directly (FIG. 13A) or 0.5, 1, 5 or 10 μM PX-12 (FIG. 13B), a drug that targets an upstream protein thioredoxin (Trx-1) known to induce HIF-1α production as well as activity. The cells were then harvested, fixed, permeabilized, and stained for HIF-1α expression before analyzing the gated lymphocyte population on the flow cytometer. The flow cytometric assay described here was able to detect the inhibition of HIF-1α upregulation mediated by both drugs in a dose dependent fashion in both donors.

EXAMPLE 8

Diagnostic Kit Composition.

Kit composition and Protocol. In order to simplify and facilitate the diagnostic techniques for monitoring or predicting therapeutic response to HIF-modulating drugs, the use of a diagnostic kit is provided. One embodiment of such a kit is described below.

The kit contains a media additive comprising a concentrated stock of a cytokine mixture to enhance cell survival upon stimulation (IL-2 and IL-15) called Component A. The kit further contains a concentrated cocktail containing a leukocyte stimulator and a hypoxia inducing agent (for example a stock consisting of T cell stimulators such as phorbol myristate acetate (PMA) and Ionophore A23187 or their equivalents; PHA or its equivalent, anti-CD3 and anti-CD28 antibodies, as well as hypoxia inducing agents such as deferoxamine (DFO) or $CoCl_2$ or their equivalents) called Component B. Component C comprises a mixture of monoclonal antibodies directed towards HIF-1α conjugated indirectly or directly with one type of fluorochrome (type A) and a T-lymphocyte marker (such as CD3, CD2, CD4 or CD8) labeled with a fluorochrome type B.

Between four to ten million peripheral blood mononuclear cells or enriched or purified T cells are required for each time point to be tested (i.e. pre and post treatment samples). Cells are freshly isolated or thawed from cryogenically preserved samples. Primary lymphocyte culture media such as AIM-V (Invitrogen, Carlsbad, Calif.) supplemented with 5% FCS is recommended for the culture of the leukocyte populations. PBMCs or enriched T cells are added at two to five million cells in 500 μL media containing 1× Component A per well of a 48 well tissue culture plate (not included in the kit). One of the two wells is designated the Control sample while the other well is designated the Activated sample. 500 μl of media containing 1× Component A is added to the Control well and 500 μl of media containing 1× Component A and 1× Component B is added to the Activated sample well. The cells are then incubated overnight (8-20 hours). The cells are harvested, fixed and permeabilized as described in the invention or by some comparable method.

In some embodiments, the responsiveness of the cells to an HIF-1α inhibitor is tested. Direct or indirect inhibitors of HIF-1α (such as PX-478 or PX-12) can be added at physiologically active concentrations to activated sample wells. These samples can be analyzed as described above for HIF-1α expression and the extent of target inhibition in vitro can be determined. In the case of monitoring in vivo patient response to therapies aimed at inhibiting HIF-1α, patient's peripheral blood leukocytes or isolated lymphocytes drawn before and after treatment can be analyzed as described above and compared to determine the extent to which the treatment is inhibiting HIF-1α. To test which patients may be responsive to a drug suppressing HIF-1α such as PX-478, whole blood drawn from patients can be spiked with physiological levels of the drug and incubated at the optimal time and temperature before isolating the peripheral blood through gradient density centrifugation or some comparable method. These cells can then be used to follow the above method to determine if the drug being tested is inhibiting HIF-1α upregulation normally induced under these conditions.

The fixed and permeabilized cells are stained as described in the invention or by some other comparable method. Such double staining is used in order to identify T lymphocytes that have increased levels of HIF-1α expression. The numbers of double stained lymphocytes are then determined by means of flow cytometry. A decreased percentage of T lymphocytes expressing HIF-1α after drug treatment compared to the before treatment sample will according to the invention identify responders to therapy.

While preferred embodiments have been described in detail, variations may be made to these embodiments without departing from the spirit or scope of the attached claims.

What is claimed is:

1. A method of identifying an individual susceptible to treatment with a HIF-1α inhibitor comprising:
   obtaining a blood sample from said individual;
   isolating peripheral blood mononuclear cells (PBMCs) from said blood sample;
   exposing said PBMCs to a leukocyte stimulating agent selected from phorbol myristate acetate, calcium ionophore, lipopolysaccharide and combinations thereof;
   measuring a level of HIF-1α protein in said PBMCs ; and
   identifying said individual susceptible to treatment, wherein elevated levels of HIF-1α protein in stimulated PBMCs compared to unstimulated PBMCs indicate said individual's susceptibility to said treatment with said HIF-1α inhibitor.

2. The method of claim 1, wherein said HIF-1α inhibitor is selected from PX-478, PX-12, 2-ME2, topotecan, camptothecin and combinations thereof.

3. The method of claim 1, wherein said HIF-1α protein level is measured using flow cytometry.

4. The method of claim 1, wherein said HIF-1α protein levels is measured using a HIF-1α antibody.

5. The method of claim 1, wherein said HIF-1α protein levels is measured by a western blot.

* * * * *

UNITED STATES PATENT AND TRADEMARK OFFICE
CERTIFICATE OF CORRECTION

| | | |
|---|---|---|
| PATENT NO. | : 7,629,128 B2 | Page 1 of 1 |
| APPLICATION NO. | : 11/379034 | |
| DATED | : December 8, 2009 | |
| INVENTOR(S) | : Kirkpatrick et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 328 days.

Signed and Sealed this

Second Day of November, 2010

David J. Kappos
*Director of the United States Patent and Trademark Office*